United States Patent [19]

Conoscenti et al.

[11] Patent Number: 4,886,496
[45] Date of Patent: Dec. 12, 1989

[54] BRONCHOSCOPIC BALLOON TIPPED CATHETER AND METHOD OF MAKING THE SAME

[76] Inventors: Craig S. Conoscenti, 17 Fawn Ridge La., Wilton, Conn. 06897; Robert A. Gandi, 299 W. 12th St., New York, N.Y. 10014; Gianfranco U. Meduri, 2 Butternut Pl., Wilton, Conn. 06897; David S. Ostrowski, R.R. 1, Box 851, N. Grosvenordale, Conn. 06255

[21] Appl. No.: 152,318
[22] Filed: Feb. 4, 1988
[51] Int. Cl.⁴ .............................................. A61M 29/00
[52] U.S. Cl. .................................... 604/96; 128/344
[58] Field of Search ................... 604/95–103; 128/344, 348.1, 325

[56] References Cited

U.S. PATENT DOCUMENTS

| | | | |
|---|---|---|---|
| 2,050,407 | 8/1936 | Wolff | 604/98 |
| 2,642,874 | 6/1953 | Keeling | 604/102 |
| 3,435,826 | 4/1969 | Forgarty | 604/96 |
| 3,448,739 | 6/1969 | Stark et al. | 128/344 |
| 3,734,100 | 5/1933 | Walker et al. | 604/103 |
| 3,833,003 | 9/1974 | Taricco | 604/96 |
| 3,880,168 | 4/1975 | Berman | 604/104 |
| 4,502,482 | 3/1985 | DeLuccia et al. | 604/100 |
| 4,762,125 | 8/1988 | Leiman et al. | 604/96 |

Primary Examiner—Dalton L. Truluck
Assistant Examiner—Denise Whelton
Attorney, Agent, or Firm—Darby and Darby

[57] ABSTRACT

A balloon tipped catheter and process for making the same is provided for the insertion into the suction channel of a bronchoscope. The balloon material is stretched across a recess formed in the catheter tubing. The stretched balloon forms an hour glass shape, thereby preventing the balloon material from becoming damaged while the catheter is being pushed through a curved bronchoscope.

2 Claims, 1 Drawing Sheet

U.S. Patent   Dec. 12, 1989   4,886,496
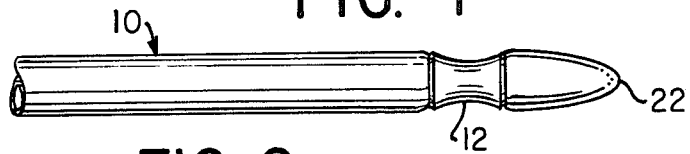
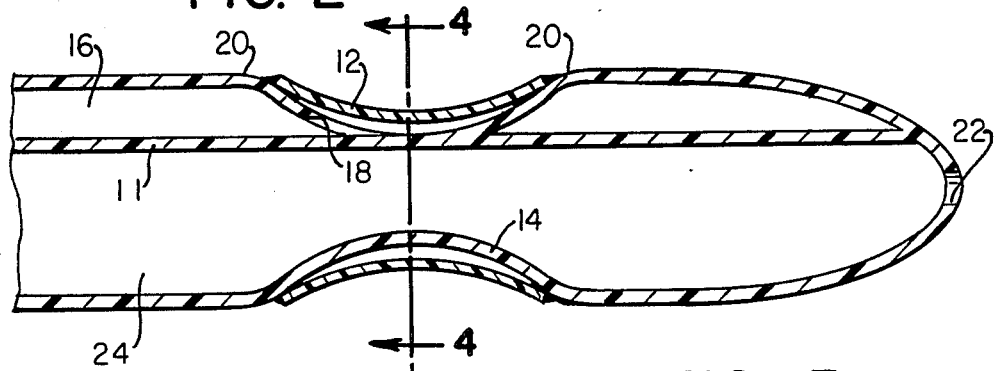
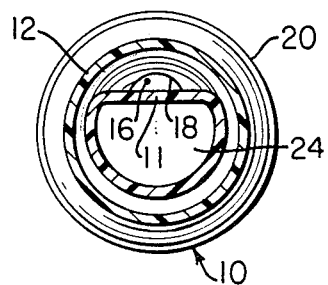
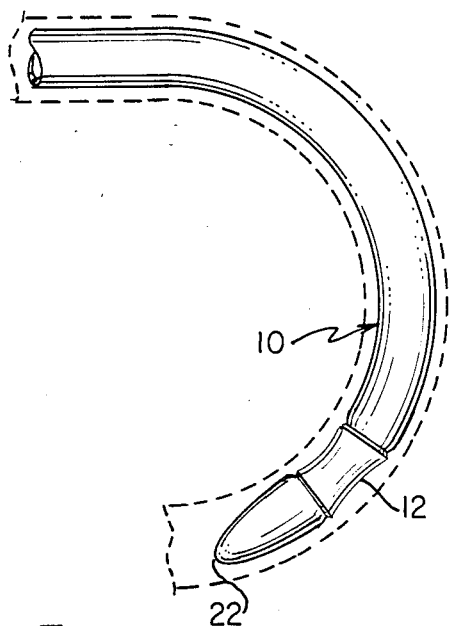
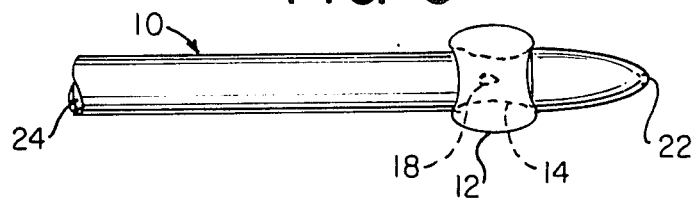

BRONCHOSCOPIC BALLOON TIPPED CATHETER AND METHOD OF MAKING THE SAME

BACKGROUND OF THE INVENTION

The invention generally relates to catheters which have inflatable balloon portions.

The invention more specifically relates to such catheters which can be inserted into and positioned by a bronchoscope.

The flexible fiberoptic bronchoscope is a triple lumen tube for containing an optic viewing fiber, a lighting passage and a suction channel. It allows both visualization of the tracheo-bronchial tree, through the viewing fiber, and sampling of secretions or tissue of the lung through the suction channel. The bronchoscope most commonly used to inspect the bronchial tree has a flexible tip which can be controlled so that inspections along branches with sharp bends may be followed more easily.

Flexible fiberoptic bronchoscopy is an invaluable tool for the diagnosis of many lung diseases. Two techniques involving the bronchoscope are bronchoalveolar lavage and tamponade of tracheo-bronchial bleeding, both of which are important in the diagnosis and management of respiratory diseases.

Bronchoalveolar lavage is the accepted technique of sampling the cellular content of the alveoli. This technique has greatly improved the understanding of many lung disorders.

In interstitial lung diseases, the cells seen in the lavage fluid represent the inflammatory and the immune effector-cell population present in the alveolar interstitium. This has allowed the characterization of different forms of "Alveolitis" and has opened a new frontier in the understanding of these disorders.

Bronchoalveolar lavage is also useful in diagnosing pulmonary infections (i.e.; pneumocystis carinii pneumonia, fungal infections, legionella, TB and CMV) and it has replaced open lung biopsy in the diagnosis of opportunistic infections in the immuno-compromised host.

Bronchoalveolar lavage is presently accomplished by wedging the tip of the flexible fiberoptic bronchoscope into a segmental bronchus. Then, injecting warm saline (37' C) through the suction channel of the bronchoscope to lavage the bronchus and alveoli. Effective retrieval of the saline lavage solution is a problem owing to the difficulties encountered in maintaining the wedge seal.

During this procedure, pressure must be applied to the bronchoscope to maintain an effective wedge seal. This pressure activates the cough reflex, disrupting the wedge seal, resulting in the leakage of the irrigating solution. Further, the applied pressure required to maintain the seal is occasionally traumatic to the bronchial mucosa.

Pulmonary hemorrhages are among the occasional complications of biopsy during bronchoscopy and can be life-threatening. During such hemorrhaging, the tip of the bronchoscope is wedged into the bronchus with the intent of limiting the bleeding to a small area of the lung. A serious inconvenience of the present modality is that the tip of the bronchoscope is obscured by blood, and the lack of visualization does not allow for adequate assessment and management. After a seal has been made, vasoconstricting agents are instilled to control the hemorrhagic process. Normal saline is instilled and aspirated to wash the blood out.

The applied wedge pressure again creates patient discomfort, activates the cough reflex and disrupts the wedge seal, thus hindering the management of the hemorrhage.

To more easily study lung related diseases and to provide a less traumatic treatment, it would be desirable to be able to insert a balloon tipped catheter through the suction lumen of the bronchoscope into the bronchial tree, thereafter use the balloon, when inflated, to seal off a particular lung subsegment instead of applying traumatic pressure to the end of the bronchoscope. There is a problem, however, in inserting a balloon tipped catheter into the appropriate channel provided by the bronchoscope. The inside wall of this channel is articulated in order to provide the necessary flexible maneuverability while positioning the scope through the passages of the lung. The articulation generates ribbed walls that tear or otherwise damage the relatively delicate elastomeric material common to prior art balloon tipped catheters while it is being pushed passed such bends.

If a damaged balloon is later positioned and inflated in the bronchial tree of a patient, the balloon may rupture, thereby breaking the isolation seal of the particular subsegment under test or treatment and reducing the quantity and quality of the retrieved specimens. When detected, the damaged catheter must be removed and a new one inserted with the same problems caused by the ribbed walls of the bronchoscope.

Although some conventional balloon tipped catheters have recessed balloons, the balloon material of such catheters does not remain recessed if the catheter tube is curved sharply. It will overlap and create wrinkles or "bulges" on the inside of its curve and can be easily damaged by the ribbed walls of a bronchoscope. An example of such a catheter having a recessed balloon is shown in U.S. Pat. No. 3,734,100.

The principal object of the present invention is to provide a balloon tipped catheter which avoids the above-identified rupturing problems.

A more specific object of the present invention is to provide a balloon tipped catheter which can be inserted through a curved suction channel of a bronchoscope without damage to the catheter or balloon. The balloon can then be positioned and inflated at a predetermined location of a lung subsegment thereby creating an effective seal which will minimize or eliminate the cough reflex and much of the patient discomfort.

SUMMARY OF THE INVENTION

In accordance with the present invention, a balloon tipped catheter has a balloon stretched into an "hourglass" recess of the catheter so that the balloon material will remain protected even when the catheter is being pushed along a sharp bend of a ribbed bronchoscope.

BRIEF DESCRIPTION OF THE DRAWINGS

FIG. 1 is a side view of the distal end of a balloon tipped catheter of the present invention;

FIG. 2 is an enlarged cross-sectional view of FIG. 1;

FIG. 3 is a cross-sectional side view of the present invention in a curved position;

FIG. 4 is a front cross-section view of the distal end of the present catheter; and FIG. 5 is a cross-sectional side view of the present invention with the balloon inflated.

DETAILED DESCRIPTION OF THE PREFERRED EMBODIMENT

A catheter tube 10 has a dividing wall 11 which forms two lumen 16 and 24 of unequal size. An "hourglass" shaped recess 14 is formed near its distal end. Communication with the sealed lung subsegment and the proximal end of the catheter is provided by the larger lumen 24, while inflation/deflation of the balloon is controlled by the smaller lumen 16.

The balloon material 12 is a section of tubing made from a conventional elastomeric material such as latex or polyurethane and is positioned around the catheter tube 10 and within the "hourglass" shaped recess 14. The balloon tubing 12 is slightly smaller in outer diameter than the outer diameter of the catheter tube 10. The cut length of the balloon tubing 12 is such that it can be stretched length wise within the recess 14 without increasing the outer diameter of the catheter tube. The edges of the balloon tubing 12 are adhered to the outer surface of the catheter tube 10 within the recess 14 using a conventional non-brittle adhesive such as a cyanoacrylate adhesive for latex balloon material and a solvent base polyurethane adhesive for polyurethane balloon material. The balloon tubing 12 is adhered within recess 14 so that it rests in a stretched condition. The stretched balloon will also form an "hourglass" shape which will ensure that the balloon tubing 12 remains protected within the recess 14 while the catheter tube 10 bends as it is maneuvered through the bronchoscope (not shown). A hole 18 is provided through the catheter tube 10 wall and within the recess 14 thereby establishing fluid communication between the balloon and the smaller lumen 16. This fluid may be gaseous, or if the smaller lumen 16 is large enough, depending on the catheter, may be a liquid.

The catheter tube 10 is shown curved in FIG. 3, similar to the degree of curvature that the catheter experiences as it travels through a typical bend in a bronchoscope channel. The stretched balloon tubing 12 slackens slightly along the inside curve 30 of the curved catheter tube 10, but remains sufficiently taut to avoid conventional recessed balloon problems such as wrinkling and "bulging" and does not increase the outer diameter of the catheter tube 10. Stretching of the balloon tubing 12 will occur along the surface following the outside curve 32, but will not increase the outer diameter of the catheter tube.

In use, the distal end of the catheter is inserted into an endoscope (such as a bronchoscope), which has been previously inserted into a patient. The endoscope is used to locate the correct position of the catheter in the patient. The endoscope may therefore be, and usually is, contorted with several sharp and gradual bends. The recessed balloon of the present catheter will not be damaged as it passes the various curves of the endoscope owing to its stretched "hourglass" recessed section. Once the balloon portion of the catheter is in position, it may be inflated using a conventional syringe (or other) with a fluid such that a seal is created between the balloon and the passage wall and the catheter is secured within the particular passageway of the patient. If a bronchoscope is used, the balloon may be inflated to seal off a damaged lung subsegment at a predetermined point along the Bronchial tree. Irrigating fluids can then be instilled and aspirated effectively and efficiently, without trauma to the patient. With the balloon in place, the bronchoscope remains clear of any blood and debris providing unimpaired visual guidance.

The catheter of the preferred embodiment has two lumen, as described, and is designed to provide protection for its balloon against the relatively rough inner walls of bronchoscopes. The recessed "hourglass" shaped stretched balloon may be employed for other catheters which are used with or without the guidance of an endoscope. The number of lumen within the catheter body tube may also vary depending on the requirements of the particular use.

The production of a balloon-tipped catheter according to FIGS. 1 and 2 is as follows. First, a length of conventional extruded catheter tbbing 10 is cut. This tubing has at least two lumen 16 and 24 and is made, for example, of conventional radiopaque polymeric material such as polyvinyl chloride or polyurethane.

The position of the balloon location is then determined relative to the distal end of the catheter tubing 10. The balloon's location varies depending on the use of the catheter. Generally, the location of the balloon will be within an inch of the distal tip 22.

The next step requires the insertion of stainless steel rods or mandrels (not shown) which are the exact shape of each individual lumen used and long enough to protect the lumen around the balloon location against the subsequent heating and recess forming steps. For the preferred catheter the rods are six to eight inches long and are inserted fully into each corresponding lumen 16 and 24 at the distal end. Then, the catheter tubing 10, with a supporting rod within each lumen 16 and 24, is carefully heated in the balloon location (recessed section) and the tubing pulled. The heater, which can be a conventional thermal forming fixture must only apply enough heat to soften the catheter tubing 10. This temperature will be between 250 to 450 degrees Fahrenheit depending on the material used and its cross-sectional thickness. By pulling the proximal and distal ends of the tubing apart, the recessed section of a desired diameter is formed. The recessed section can also be formed with a heat forming mold or other conventional methods. The diameter and length of this recessed section varies with the type of catheter desired and the thickness of the balloon material used.

The lumen supporting rod for the smaller lumen 16, through which the balloon is inflated and deflated, is removed and a conventional atraumatic tapered distal end is formed and the distal end of the unsupported balloon fluid communication lumen 16 is sealed by a conventional means such as using a heated taper-forming die. After the formed tip has cooled, the support rod (or rods) for the larger lumen 24 is then removed leaving a distal hole (or holes) through which communication is provided to the sealed lung subsegment of the patient.

A hole 18 no larger then the diameter of the lumen 16 is then made near the middle of the recessed section 14. The hole is made by any conventional process such as melting, die cutting or drilling.

The balloon material, which is a conventional elastomeric extruded tubing 12, such as latex or polyurethane, is cut to a length 25% shorter than the recessed section of the catheter tube 10 and positioned into the recessed section 14 by sliding it over the distal end 22. Although this position varies depending on the size and shape of the recessed section 14, it is approximately ⅛ inch from the point 20 where the recessed slope begins. One end of the balloon is then everted and the appropriate adhesive applied to the catheter. The everted section of the balloon is then rolled back over the adhesive and allowed to air cure. The balloon tubing is then stretched across the concave section of the catheter and held by frictional resistance while the remaining un-glued end of the balloon tubing is everted and the adhesive applied. This everted end is similarly rolled back onto the adhesive and allowed to air cure before the frictional resistance is removed.

It is the stretching of the elastomeric material which causes the balloon to assume a concave "hourglass" shape which protects it during its introduction into the patient through an endoscope.

What is claimed is:

1. A flexible balloon tipped catheter designed to minimize trauma to the balloon when inserted into a channel of a flexible endoscope which, in use, assumes intricate convoluted configurations, comprising:
    a catheter tube having a distal end and at least one lumen;
    a concave recessed section formed on the exterior surface of said catheter tube located at said distal end;
    an inflatable elastomeric balloon material adhered under tension within said recessed section such that said balloon material remains in said recess and follows the concavity of said recess when said catheter proceeds through said convoluted configurations of the channel, thus preventing mechanical trauma to said balloon material from contact between said balloon material and the wall surfaces of said channel;
    means for fluid communication between said balloon portion and one of said lumen.

2. A method for atraumatically sealing off a passageway to a subsection of the bronchial tree of a patient using a flexible, fiber optic bronchoscope and a balloon tipped catheter, the steps comprising:
    inserting the flexible, fiber optic bronchoscope under continuous visualization into said passageway of the patient, said bronchoscope having a channel through which a catheter may be passed;
    using said fiber optics of said bronchoscope to locate a position along said passageway whereby the seal is to be made;
    inserting a balloon tipped catheter into said channel of said bronchoscope, said catheter having a recessed balloon such that said balloon is protected from damage by the inner surface of said channel;
    positioning visually said catheter using the fiber optics of said bronchoscope such that said balloon is located at said sealing position in said passageway;
    inflating said balloon such that the balloon creates a seal within said passageway, thereby sealing said subsection of said bronchial tree, said catheter providing fluid communication into and out from said sealed subsection.

* * * * *